United States Patent [19]

Clark

[11] 4,235,373
[45] Nov. 25, 1980

[54] FLUID DISPENSER

[75] Inventor: Peter J. Clark, Hemel Hempstead, England

[73] Assignee: Strattwell Developments Limited, London, England

[21] Appl. No.: 841,599

[22] Filed: Oct. 12, 1977

[30] Foreign Application Priority Data

Oct. 12, 1976 [GB] United Kingdom ............... 42308/76

[51] Int. Cl.³ ............................................. A61L 9/04
[52] U.S. Cl. ....................................... 239/34; 239/70; 239/120
[58] Field of Search ........................ 239/34, 37, 38, 43, 239/51, 120, 121, 122, 326, 70; 261/112

[56] References Cited

U.S. PATENT DOCUMENTS

| 2,047,973 | 7/1936 | Lawton et al. | 239/38 X |
| 2,991,912 | 7/1961 | Thomas et al. | 239/70 X |
| 3,018,056 | 1/1962 | Montgomery | 239/70 |
| 3,158,081 | 11/1964 | Frost | 239/70 X |
| 3,203,594 | 8/1965 | Jones | 222/70 |
| 3,330,481 | 7/1967 | Dearling | 239/326 X |
| 3,388,834 | 6/1968 | Hart | 239/70 X |
| 3,397,646 | 8/1968 | Allsopp, Jr. | 222/70 X |
| 3,589,563 | 6/1971 | Carragan et al. | 239/70 X |
| 3,739,944 | 6/1973 | Rogerson | 239/70 X |
| 3,790,081 | 2/1974 | Thornton et al. | 239/59 X |
| 3,972,473 | 8/1976 | Harrison | 239/34 |
| 4,084,732 | 4/1978 | Dearling | 239/34 X |

FOREIGN PATENT DOCUMENTS 335320 9/1930 United Kingdom .
1424697 2/1976 United Kingdom .
1443346 7/1976 United Kingdom .

Primary Examiner—Robert W. Saifer
Attorney, Agent, or Firm—Cushman, Darby & Cushman

[57] ABSTRACT

A fluid dispenser comprises a container for fluid having release means coupled with the container which is operatively coupled with an actuating means for effecting periodic operation of the release means to effect release of a portion of the fluid in the container to an outlet. A convection chamber has a lower aperture for permitting entry of air and an upper aperture for permitting exit of air. The chamber is provided with a downwardly extending inner surface which is adsorbent and which is arranged to receive fluid portions from the outlet. The surface permits dispersion of the fluid downwardly on the surface to allow vaporization of the fluid in the convection air flow.

9 Claims, 3 Drawing Figures

FLUID DISPENSER

BACKGROUND OF THE INVENTION

This invention relates to a fluid dispenser which is actuable periodically and automatically to dispense fluid for dispersal into the atmosphere.

Fluid dispensers are known to us which employ a mechanism operated by an electric motor which effects periodic operation of an aerosol spray container to spray a perfumed aerosol into the atmosphere of a room. Such dispensers provide a very quick and noticable fragrance in the room but the effect reduces very quickly in the period before the next actuation of the mechanism. This is disadvantageous and although the effect can be reduced by reducing the time intervals this is not practical where battery operation of the electric motor is involved in view of the reduced battery life which would result.

Dispensers of the wick type are also known to us in which a wick dips into a container of a perfumed volatile liquid and has one end exposed to the atmosphere. The liquid in the container is absorbed by the wick and is dispersed therefrom by vaporisation. Such an arrangement provides a continuous dispersion of fluid into the atmosphere and provides a substantially constant fragrance in a room. It has been discovered that such a continuous fragrance is less pleasing to occupiers of a room than the previously mentioned system in which the fragrance is periodically boosted.

SUMMARY OF THE INVENTION

This invention seeks to provide a fluid dispenser in which the disadvantages of the before mentioned dispensers are obviated or reduced.

According to the invention there is provided a fluid dispenser comprising a container for fluid, release means coupled with the container which release means has an outlet for said fluid and is operable to effect release of a portion of said fluid from the container via the outlet, actuating means operatively coupled with the release means for effecting periodic operation of the release means, and a convection chamber having a lower aperture for entry of air and an upper aperture for exit of air which convection chamber is provided with a downwardly extending inner absorbent surface arranged to receive the released portion of said fluid to permit dispersion downwardly on the surface and vaporisation of the fluid into the convection air flow, said downwardly extending surface being provided with a progressing series of generally transversally extending individual channels each having at least one centrally depressed chevron shape as seen in front elevation, and a plurality thereof having at least two transversally adjacent centrally depressed chevron shapes which adjoin at an apex; the central depressions of said chevron shapes in a plurality of instances of adjacent paired ones of said channels being transversally staggered, so that as a released fluid portion is received on said internal surface it is conducted laterally leftwards and rightwards toward said central depressions and overflows down said internal surface from upper ones to lower ones of said channels.

The release means may be a pump and is preferably of the metering type. Alternatively, the container may be pressurised such that fluid is delivered upon actuation of a release means in the form of a release valve, for example an aerosol container. Preferably the release valve is of the metering type.

The actuating means may comprise an electrically powered pump or valve actuator actuated periodically by a timing device and is preferably battery operated.

Preferably the release means is arranged to spray the portion of released fluid onto the surface.

In one particularly advantageous version of the invention there is provided a fluid dispenser comprising a container for a fluid, a pump coupled with the container and having an outlet spray nozzle, an actuator for said pump having an actuator mechanism operable by means of an electric motor, a timer connected in circuit with the electric motor and effective to actuate the motor periodically, a convection chamber having a lower aperture for entry of air and an upper aperture for exit of air to permit inflow and outflow of air by convection, the chamber having an aperture aligned with said outlet spray nozzle and internal surface generally vertically oriented and provided with a vertically progressing series of generally transversally extending individual channels each having at least one centrally depressed chevron shape as seen in front elevation, and a plurality thereof having at least two transversally adjacent centrally depressed chevron shapes which adjoin at an apex; the central depressions of said chevron shapes in a plurality of instances of vertically adjacent paired ones of said channels being transversally staggered, so that as a released fluid portion is sprayed on said internal surface, droplets thereof are conducted laterally leftwards and rightwards toward said central depressions and overflow down said internal surface from upper ones to lower ones of said channels.

BRIEF DESCRIPTION OF THE DRAWINGS

In order that the invention and its various other preferred features may be understood more easily, an embodiment thereof will now be described, by way of example only, with reference to the drawings in which.

DESCRIPTION OF THE PREFERRED EMBODIMENTS

Figure 1:
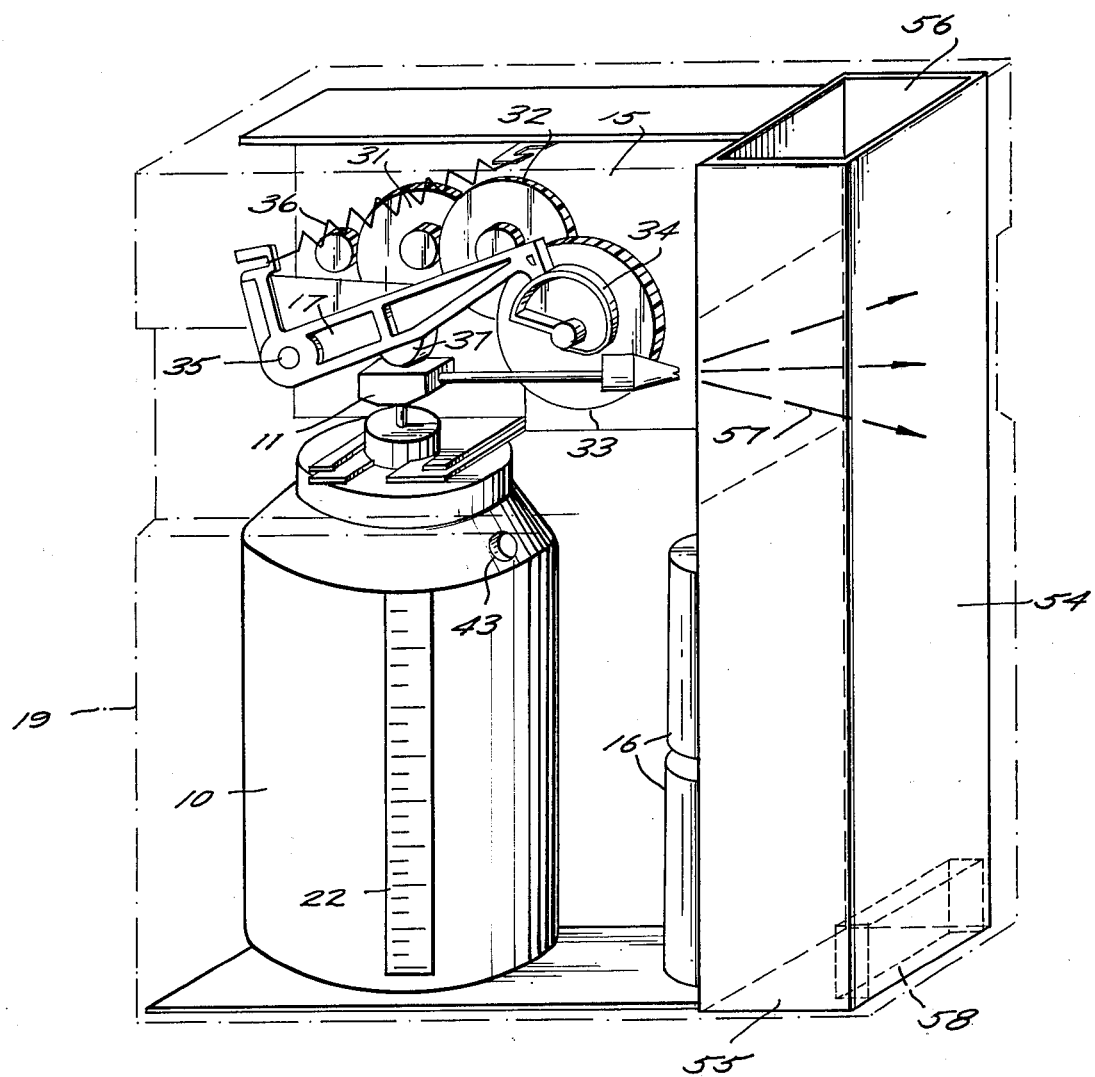
FIG. 1 is an elevational view, from one side and towards one end of a fluid dispenser constructed in accordance with the invention.
Figure 2:
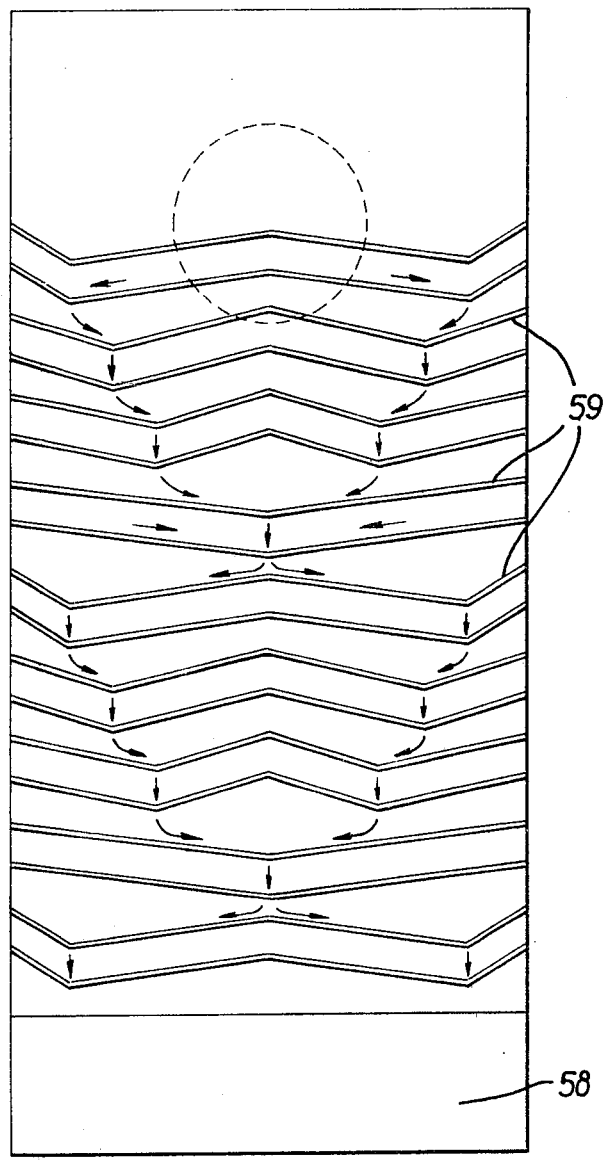
FIG. 2 is a plan view of an inner face of a preferred form of adsorbent surface for the convection chamber of the embodiment of FIG. 1

In the drawing of FIG. 1 a sealed container 10 is filled with an air freshener liquid containing a perfuming or deodorizing agent. The container is fitted with a removable pump 11 of the plunger type in which a measured amount of liquid is delivered to an outlet pipe 12 each time the plunger is depressed.

A housing 19 is provided with an elongate metal convection chamber 54 in the form of a vertical chimney of rectangular configuration. The chamber extends from the bottom to the top of the housing and has an inlet end 55 at the bottom and an outlet end 56 at the top through which air passes by convection. In one side of the chamber 54 and towards the top there is provided an aperture 57 which is in alignment with the outlet from the pump 11 which in this case is fitted with a spray nozzle. Actuation of the pump which in this case is of the metering type is effected by an actuating mechanism as will be described and results in a spray of fluid onto the adsorbent inner surface of the convection chamber.

The metering pump is actuated by an electrically driven actuator 15 operated by dry batteries 16 and having an actuating arm 17. The actuator is operated periodically by a timer 18 arranged to effect a single or several depressions of the plunger of the pump 11 during short dispensing periods alternating with longer non dispensing time periods.

The actuator has a reduction gearing employing gear wheels 31, 32 and 33, the wheel 31 being driven by an electric motor (not shown) and the final low speed gear being provided with a cam 34 which serves to actuate the pump 11. The arm 17 is pivoted at one end by means of a pivot 35 and is urged in a clockwise direction as viewed in the drawing by means of a strong spring 36, such that its end remote from the pivot engages the surfaces of the cam 34. The arm 17 is provided at a point part way therealong with an engagement portion 37 which engages with the plunger of the pump 11. As can be seen from the drawing the cam has an abrupt edge and when the gear 33 is rotates in a clockwise direction, as viewed in the drawing, the arm is moved suddenly under the action of the spring to depress the plunger of the pump when the end of the arm 17 drops over the abrupt edge on the cam. This operation is effected periodically by the timer.

The container 10 has a transparent graduated scale 22 indicating, by the level of liquid, the number of days continuous operation that can be effected before the contents are used up. The capacity of the container 10 can be arranged to be sufficient to cover the life of the batteries and an extended period of automatic trouble free operation is envisaged. This results in ease of maintenance in that batteries and liquid can be replaced at the same time.

In operation some of the spray is released immediately as a vapour from the convection chamber and some of the spray coats the inner surface with fine droplets of fluid which droplets are gradually dispersed by vaporisation into the passing air at a rate dependent on the volatility of the contents of the fluid. This system has been found to be particularly effective and avoids any need to provide additional adsorbent or absorbent screens or pads as the inner surface of the metal convection chamber forms an adsorbent surface. However in some circumstances it is advantageous to provide a pad of absorbent material shown in the drawing as 58 at the bottom of the convection chamber. This prevents fluid dripping from the bottom and provides a further surface from which vaporisation takes place. Clearly the convection chamber can be formed of any other suitable material e.g. plastics and the inner surface may be etched or otherwise modified to increase its surface area to improve the adsorbency of the surface. It has been found that a particularly advantageous dispersion and holding effect for the fluid can be provided by means of carefully designed engraved channels which are of repetative chevron shape and extend transversely of the inner wall of the convection chamber opposite the aperture 57. Such a configuration is shown in FIG. 10. It will be seen that the points of the chevron channels 59 which are located downwardly are staggered in a direction transversely of the plate. The area of impact of the spray is indicated by the dotted line and fluid on the plate runs downwardly into the channels and is spread alternately inwardly and outwardly of the plate by being guided along the channels to a chevron point, flowing downwardly from the chevron point into the channel below and along that channel to the next chevron point etc. This procedure continues along the channels from top to bottom of the plate with the fluid being directed backwards and forwards across the plate. The direction of flow of fluid is shown by arrows in the drawing. The grooves can be provided in the plate by any suitable means but engraving has been found to be particularly advantageous in that the impression left by the engraving tool tends to slow down the movement of fluid.

Figure 3:
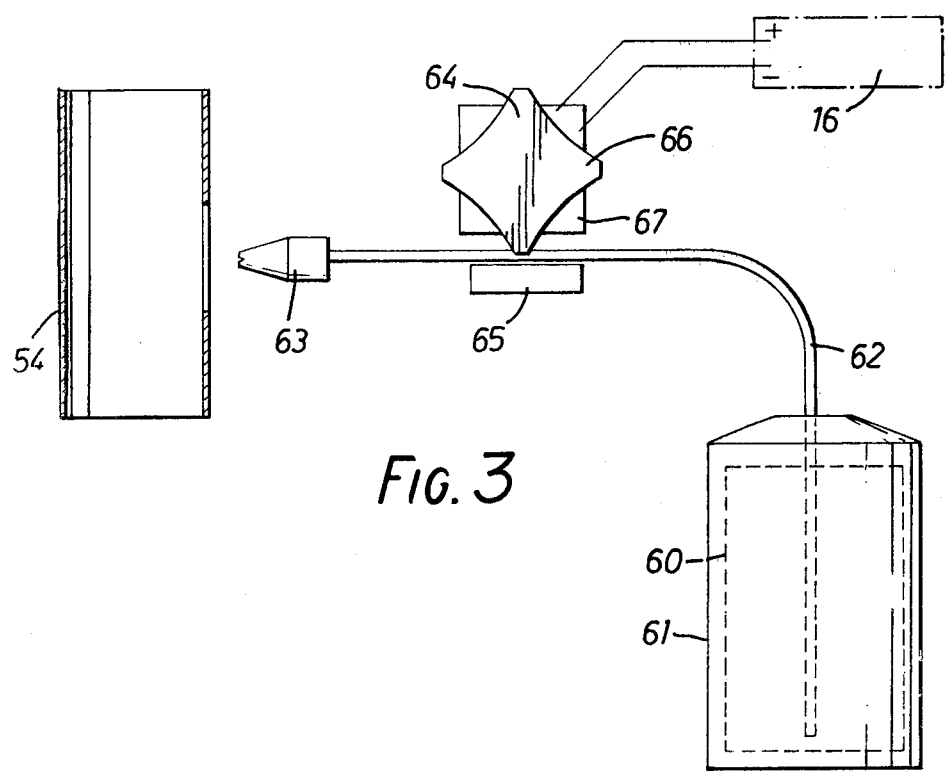
FIG. 3 is a schematic illustration of a dispenser employing a peristaltic pump.

The diagram of FIG. 3 illustrates the use of a peristaltic pump configuration with the convection chamber 54 arrangement of FIG. 1. In this embodiment a collapsible plastics bag 60 for the fluid is contained within a container 61. A flexible supply pipe 62 which may be of for example plastics tube extends from within the bag 60 and is preferably sealed thereto at the exit from the bag. Such bags with pipes attached are used by the blood transfusion service and have been found particularly suitable for this application. The pipe 62 is fitted at one end with a spray nozzle 63 and is routed between rotatable impeller 64 and a support 65. The impeller has a number of projections 66 and in the illustrated embodiment has four projections which are formed by the bevelled corners of an impeller of substantially square cross sectional form. The impeller is rotated periodically by means of a motor 67 powered by batteries 16 in response to a timer (not shown) in the manner previously described in relation to earlier described embodiments. Rotation of the impeller 66 in a clockwise direction as illustrated in the drawing causes the edges 66 to be wiped consecutively over the tube 62 and compress the tube bore between the edge and the support 65 causing flow of fluid along the tube towards the spray nozzle 63 by peristaltic action and spraying of fluid into the convection chamber 54.

Tests have shown that the power consumption for a motor to operate a peristaltic pump arrangement of the configuration of FIG. 3 is considerably less than that required in the mechanisms of the embodiments of FIG. 1 and this is particularly advantageous when dry battery power sources are employed for the operation. Accordingly, it can advantageously be used to replace the mechanism used in the embodiments of FIG. 1.

The embodiments described are susceptible of various modifications as follows:

To avoid changing the container when partly used the reservoir may be arranged to be refillable in situ. This is effected by means of a filling aperture or non return filling valve 43 e.g. a silicon rubber seal at the top of the container. The container can then be topped up advantageously by means of a large syringe, such as a hypodermic syringe in the case of the silicon rubber seal, which has reverse calibrations to those on the container. In this way filling of the syringe to the same number as on the container will provide sufficient liquid to refill the container.

Instead of employing a container 10 fitted with a pump 11 it is possible to substitute a pressurised container e.g. an aerosol container preferably having a metering outlet valve. However, in view of the controversy relating to the use of fluorocarbon propellents in such containers, which propellents are thought to harm the earth ozone layer, it is preferred to avoid such arrangements.

A plurality of adsorbent absorbent surface can be provided to enhance the evaporation of the liquid.

The timer and actuator may be operated by other means than battery power e.g. mains electricity or clockwork power.

The dispenser can be employed to dispense any evaporable liquid which may contain any agent capable of transmission with the vapour during evaporation. Some possible agents are perfumes, deodorisers, bactericides pesticides.

To enhance the flow of air through or past the adsorbent or absorbent surface a motorised fan may be provided and this can be arranged to operate continuously or periodically.

It will be understood that the above description of the present invention is susceptible to various modification changes and adaptations.

What is claimed is:

1. A fluid dispenser comprising a container for fluid, release means coupled with the container which release means has an outlet for said fluid and is operable to effect release of a portion of said fluid from the container via the outlet, actuating means operatively coupled with the release means for effecting periodic operation of the release means, and a convection chamber having a lower aperture for entry of air and an upper aperture for exit of air which convection chamber is provided with a downwardly extending inner adsorbent surface arranged to receive the released portion of said fluid to permit dispersion downwardly on the surface and vaporisation of the fluid into the convection air flow, said downwardly extending surface being provided with a progressing series of generally transversally extending individual channels each having at least one centrally depressed chevron shape as seen in front elevation, and a plurality thereof having at least two transversally adjacent centrally depressed chevron shapes which adjoin at an apex; the central depressions of said chevron shapes in a plurality of instances of adjacent paired ones of said channels being transversally staggered, so that as a released fluid portion is received on said internal surface it is conducted laterally leftwards and rightwards toward said central depressions and overflows down said internal surface from upper ones to lower ones of said channels.

2. A fluid dispenser as claimed in claim 1, wherein said release means comprises a metering valve for delivering a predetermined dose of said fluid via said outlet at each actuation of said actuating means.

3. A fluid dispenser as claimed in claim 1, wherein said release means comprises a pump.

4. A fluid dispenser as claimed in claim 3, wherein said pump is a peristaltic pump.

5. A fluid dispenser as claimed in claim 1, wherein said actuating means comprises a mechanism operated by an electric motor and a timer connected in circuit with the electric motor and effective to trigger the motor operation periodically.

6. A fluid dispenser as claimed in claim 1, wherein said release means is arranged to spray said portion of released fluid onto said adsorbent surface.

7. A fluid dispenser as claimed in claim 1 wherein said convection chamber has an internal surface which forms said adsorbent surface.

8. A fluid dispenser as claimed in claim 1 comprising spray means for releasing said fluid portions onto said internal surface in the form of a spray.

9. A fluid dispenser comprising a container for a fluid, a pump coupled with the container and having an outlet spray nozzle, an actuator for said pump having an actuator mechanism operable by means of an electric motor, a timer connected in circuit with the electric motor and effective to actuate the motor periodically, a convection chamber having a lower aperture for entry of air and an upper aperture for exit of air to permit inflow and outflow of air by convection, the chamber having an aperture aligned with said outlet spray nozzle and internal surface generally vertically oriented and provided with a vertically progressing series of generally transversally extending individual channels each having at least one centrally depressed chevron shape as seen in front elevation, and a plurality thereof having at least two transversally adjacent centrally depressed chevron shapes which adjoin at an apex; the central depressions of said chevron shapes in a plurality of instances of vertically adjacent paired ones of said channels being transversally staggered, so that as a released fluid portion is sprayed on said internal surface, droplets thereof are conducted laterally leftwards and rightwards towards said central depressions and overflow down said internal surface from upper ones to lower ones of said channels.

* * * * *